United States Patent
Kovacs et al.

[11] Patent Number: 5,833,603
[45] Date of Patent: Nov. 10, 1998

[54] IMPLANTABLE BIOSENSING TRANSPONDER

[75] Inventors: Gregory T. A. Kovacs, Stanford, Calif.; Terry R. Knapp, Neuchâtel, Switzerland

[73] Assignee: LipoMatrix, Inc., Virgin Islands (Br.)

[21] Appl. No.: 614,519

[22] Filed: Mar. 13, 1996

[51] Int. Cl.$^6$ .................................................. A61B 10/00
[52] U.S. Cl. .............................................................. 600/317
[58] Field of Search ..................................... 128/630–633, 128/637, 903; 600/300, 382, 317

[56] References Cited

U.S. PATENT DOCUMENTS

| | | | |
|---|---|---|---|
| 3,229,684 | 1/1966 | Nagomo et al. | 128/631 |
| 3,399,667 | 9/1968 | Nishimoto et al. | 128/631 |
| 3,576,554 | 4/1971 | Temps et al. | |
| 3,839,708 | 10/1974 | Bredesen et al. | |
| 3,853,117 | 12/1974 | Murr. | |
| 3,893,111 | 7/1975 | Cetier | 128/631 |
| 3,949,388 | 4/1976 | Fuller. | |
| 3,972,320 | 8/1976 | Kazman | 128/903 |
| 4,041,954 | 8/1977 | Ohara | 128/630 |
| 4,160,971 | 7/1979 | Jones et al. | |
| 4,262,632 | 4/1981 | Hanton et al. | |

(List continued on next page.)

FOREIGN PATENT DOCUMENTS

| | | |
|---|---|---|
| 619 101 A1 | 10/1994 | European Pat. Off. . |
| 0 646 313 A1 | 4/1995 | European Pat. Off. . |
| 2 680 672 | 3/1993 | France . |
| 43 41 903 A 1 | 6/1995 | Germany . |
| 2 258 589 | 2/1993 | United Kingdom . |
| WO8704900 | 8/1987 | WIPO . |
| WO 92/07505 | 5/1992 | WIPO . |
| WO9207505 | 5/1992 | WIPO . |

OTHER PUBLICATIONS

Copy of search results from DIOG Database.
trovan™ Electronic Identification System, Ltd. brochure for Model—ID 100, entitled "Implantable Transponder"; 4 pp.

Hughes Identification Device brochure entitled "Injectable Transponder Small Size", 6 pp.

A low power multi–sensor interface for injectable microprocessor–based animal monitoring system by P. Wouters, M. De Cooman, D. Lapadatu and R. Puers. *Sensors and Actuators*, 1994, pp. 198–206.

*Primary Examiner*—William E. Kamm
*Attorney, Agent, or Firm*—Howell & Haferkamp, L.C.

[57] ABSTRACT

A biosensing transponder for implantation in an organism including a human comprises a biosensor for sensing one or more physical properties related to the organism after the device has been implanted, including optical, mechanical, chemical, and electrochemical properties, and a transponder for wirelessly transmitting data corresponding to the sensed parameter value to a remote reader. Disclosed embodiments utilize temperature sensors, strain sensors, pressure sensors, magnetic sensors, acceleration sensors, ionizing radiation sensors, acoustic wave sensors, chemical sensors including direct chemical sensors and dye based chemical sensors, and photosensors including imagers and integrated spectrophotometers. The transponder includes an energy coupler for wirelessly energizing the device with a remote energy source, and a control circuit for controlling and accessing the biosensor and for storing identifying data. The energy coupler can be an inductive circuit for coupling electromagnetic energy, a photoelectric transducer for coupling optical energy, or a piezoelectric transducer for coupling ultrasonic energy. The control circuit can be configured to delay, either randomly or by a fixed period of time, transmission of data indicative of the sensed parameter value to thereby prevent a data collision with an adjacent like device. Methods for using an implantable biosensing transponder include the steps of associating the device with an implant, including temporary implants, prostheses, and living tissue implants, physically attaching the device to a flexible catheter, sensing parameter values in an organism, and transmitting data corresponding to the sensed parameter values to a remote reader.

21 Claims, 5 Drawing Sheets

U.S. PATENT DOCUMENTS

| | | |
|---|---|---|
| 4,361,153 | 11/1982 | Slocum et al. . |
| 4,399,821 | 8/1983 | Bowers . |
| 4,531,526 | 7/1985 | Genest . |
| 4,618,861 | 10/1986 | Gettens et al. . |
| 4,703,756 | 11/1987 | Gough et al. . |
| 4,730,188 | 3/1988 | Milheiser . |
| 4,746,830 | 5/1988 | Holland . |
| 4,752,115 | 6/1988 | Murray, Jr. et al. ............ 128/637 |
| 4,854,328 | 8/1989 | Pollack . |
| 4,863,470 | 9/1989 | Carter . |
| 4,875,483 | 10/1989 | Vollmann . |
| 4,992,794 | 2/1991 | Brouwers . |
| 5,010,893 | 4/1991 | Sholder . |
| 5,012,286 | 4/1991 | Kawano et al. . |
| 5,028,918 | 7/1991 | Giles et al. . |
| 5,036,869 | 8/1991 | Inahara . |
| 5,041,826 | 8/1991 | Milheiser . |
| 5,084,699 | 1/1992 | DeMichele . |
| 5,095,309 | 3/1992 | Troyk et al. . |
| 5,211,129 | 5/1993 | Taylor et al. . |
| 5,218,343 | 6/1993 | Stobbe et al. . |
| 5,235,326 | 8/1993 | Beigel et al. . |
| 5,300,120 | 4/1994 | Knapp et al. . |

IMPLANTABLE BIOSENSING TRANSPONDER

BACKGROUND AND SUMMARY OF THE INVENTION

Passive transponders, i.e., transponders containing no on-board power sources, while available for many years, have only recently been applied to humans. These transponders may be encoded and implanted in a patient, and subsequently accessed with a hand held electromagnetic reader in a quick and non-invasive manner. Due to the small size of the transponder, the patient does not sense any discomfort or even the presence of the transponder. The companion hand held electromagnetic reader emits a low frequency magnetic field to activate the passive transponder and thereby cause it to transmit its encoded data to the reader. Hence, no battery or other source of electrical power need be included in the passive transponder, further reducing the size of the transponder and making it more suitable for implantation.

As disclosed in prior filed U.S. patent applications including Ser. No. 08/461,117 filed on Jun. 5, 1995 (now U.S. Pat. No. 5,725,578), Ser. No. 08/375,811 filed on Jan. 20, 1995, Ser. No. 07/938,833 filed on Aug. 31, 1992 (now abandoned), Ser. No. 08/221,706 filed on Apr. 1, 1994 (now U.S. Pat. No. 5,678,288), and Ser. No. 934,785 filed on Aug. 24, 1992 (now U.S. Pat. No. 5,300,120), the disclosures of all of which are incorporated herein by reference, passive transponders can be implanted in the patient and encoded with data pertaining to the patient's identification and medical history or conditions, as well as data pertaining to the transponder itself. Passive transponders can also be used with other implants, including temporary implants, living tissue implants, and medical prostheses, for storing data pertaining to the other implant. The stored data may be directly representative of the patient or implant data, or may be a unique tag for accessing an external database to obtain the desired information.

Although passive transponders have not previously been used for remotely accessing physiological information related to a patient or organism, a team at the University of Michigan has developed implantable intramuscular stimulators based on electromagnetically coupled energy and partial glass encapsulation. A hemicylinder of glass is bonded to a silicon substrate containing electronics and stimulating electrodes. After implantation, electromagnetic energy is transmitted through a patient's tissue to energize the device. The coupled energy is stored in the device in an on-board capacitor which discharges upon receiving a coded instruction to thereby stimulate a local muscle. However, this device is incapable of detecting, measuring, and relaying physiologic or other measurements to an external reader, and is solely concerned with delivering stimulation pulses to muscle tissues.

There is also a virtually limitless variety of sensors presently available for detecting almost any physical property related to an organism, including optical, chemical, and electrochemical properties. Examples include temperature sensors for detecting the temperature of an organism and chemical sensors for detecting the presence or absence of particular chemicals, including direct chemical sensors and dye based chemical sensors that operate by detecting, with a photosensor, changes in an optical property of a dye.

Another type of sensor is the spectrophotometer for performing precise optical measurements. A region of tissue, gas, or fluid of interest is illuminated with an optical energy source having a known spectrum, and the light is broken into its constituent wavelengths, such as with a prism or grating. An array of one or more photosensors is positioned at the output of the prism or grating so that each photosensor corresponds to a predetermined range of wavelengths. By comparing the detected spectrum and the spectrum of illumination, the optical spectrum of absorption or reflection (and thus related chemical or physiologic properties), depending upon the path of light, can be determined for the tissue, gas, or fluid of interest.

An integrated spectrophotometer, designed by Stanford University, is described in U.S. patent application Ser. No. 377,202 filed Jan. 24, 1995, now abandoned, the disclosure of which is incorporated herein by reference. As described therein, a spectrophotometer grating is fabricated by electron beam exposure of a thin layer of polymethalmethacrylate (PMMA) on a thin, i.e., approximately 100 angstrom, layer of chromium on a quartz or glass optical substrate. When the PMMA is developed, unwanted chromium is exposed and can be removed using a chemical etch. The desired optical pattern is then present in the form of patterned chromium. This fabrication process is carried out such that a single substrate can readily yield dozens to hundreds of gratings. The optical substrate is sawed into individual gratings, which are then mounted above linear arrays of photosensors, such as photodiodes or phototransistors for visible and near-infrared light, or infrared sensors for longer wavelengths. Each detector thus receives light in a particular wavelength range, as determined by the grating.

A key aspect of the integrated spectrophotometer, in addition to being fabricated through micromachining techniques, is that a given grating pattern can be computed using the known absorption spectrum of the compound of interest. The essential process comprises computing the inverse Fourier transform of the absorption spectrum and generating a pseudo-continuous-tone grating function using half-toning techniques and/or shallow etching of the quartz substrate to provide phase information, the former often used in laser printers, to simulate continuous tones. A grating pattern computed in this manner can serve as a matched filter to the optical spectrum of transmission or reflection, depending upon whether light is passing through or is reflected from a substance or tissue before reaching the spectrophotometer, respectively.

As technology progresses, and a greater number of sensors of decreasing sizes become available, more and more sensors become amenable to implantation into living organisms, including both animals and humans, so that remote assessments of physical properties can be accomplished. For example, U.S. Pat. No. 4,854,328 to Pollack discloses an animal monitoring telltale and information system comprising an implantable transmitter which includes a temperature sensor and a power supply. The sensor monitors the temperature of the animal and, upon sensing a predetermined threshold value, transmits a signal indicative thereof to a remote receiver. However, because the implantable transmitter requires a power source, such as a battery, to power the transmitter and sensor, the device is useful for only a limited period of time after implantation. Moreover, after the on-board power source is depleted, an invasive operation, in addition to the initial implantation, will have to be made to remove the device from the animal and to replace it with a like device.

What is needed is an implantable device that can sense one or more physiologic parameter values, and that can be remotely accessed by, for example, a hand held reader to obtain the sensed parameter values in a non-invasive manner. No on-board power sources should be utilized so that the device will never need to be removed from an implantation site in order to replace an electrical power source, and can therefore remain implanted for an indefinite period of time. Instead, the remote reader should be used to energize the device, such as with electromagnetic energy, to thereby cause the device to sense the physiologic parameter values and transmit data representative thereof to the remote reader.

The inventors herein have succeeded in designing and developing a biosensing transponder, and methods of use thereof, for implantation in an organism. The biosensing transponder includes a biosensor for detecting one or more physical properties related to the organism, including optical, mechanical, chemical, and electrochemical properties, and a transponder for energizing the device with a remote reader and for transmitting data corresponding to the sensed physical property to the remote reader. Due to its small size and the absence of a need for an on-board electrical power source, the biosensing transponder of the present invention is particularly suitable for human implantation, and can remain implanted for an indefinite period of time.

Nearly any type of sensor can be utilized in the biosensing transponder of the present invention, limited only by the size of the particular sensor and the available space at the implantation site. The biosensing transponder can also be used for sensing physical parameter values related to other implants in a patient, including temporary implants, living tissue implants, and medical prostheses, in addition to sensing physical parameter values directly related to the patient's organs and tissue.

Some examples of implantable biosensing transponders constructed according to the present invention include devices for monitoring blood chemistry, such as sugar, pH, oxygenation, and hemoglobin levels, devices for monitoring blood circulation through transplanted living tissue, devices for monitoring accelerations of tissues, devices for monitoring therapeutic or unintentional doses of ionizing radiation, devices for monitoring strain forces on prostheses such as artificial heart valves and joint replacement systems, and devices for monitoring the degree of fibrosis around cosmetic implants. In every case, the biosensing transponder is energized by a remote reader for performing the particular sensing or monitoring function, and for transmitting data indicative thereof to the remote reader.

By providing a means for remotely and non-invasively obtaining physiological data related to a patient, the biosensing transponder of the present invention contributes to lower patient and healthcare provider risks, and should contribute to lower patient and healthcare provider costs. The biosensing transponder is particularly suitable for patients having a personal or family history of health problems for which early detection of an onset can be extremely beneficial and oftentimes lifesaving.

As stated above, the biosensing transponder of the present invention includes a biosensor and a transponder. The transponder includes an energy coupler for wirelessly coupling energy from a remote energy source, and for wirelessly transmitting data corresponding to the parameter value sensed by the biosensor to the remote reader. Preferred energy couplers include: inductive circuits for energizing the device with a remote electromagnetic energy source and for electromagnetically transmitting data to a remote reader; photoelectric transducers for energizing the device with a remote optical energy source and LEDs for optically transmitting data to a remote reader; and piezoelectric transducers for energizing the device with a remote ultrasonic energy source and for ultrasonically transmitting data to a remote reader. Such transducers can also be used in combination where it is desirable to receive power through one type of transducer and transmit data with another.

These various types of energy couplers are also suitable for use with previously designed transponders, in addition to the biosensing transponders of the present invention. Where a piezoelectric transducer is utilized along with a transponder capsule, the transducer can be bonded to an interior wall of the capsule, or can simply be placed within the capsule and the capsule filled with an incompressible fluid for coupling ultrasonic energy to the piezoelectric transducer.

The transponder utilized in the present invention also includes a control circuit for performing a variety of functions depending upon the specific implementation. For example, the control circuit can be configured to delay, either randomly or by a fixed or programmed period of time, the transmission of data to the remote reader to prevent the biosensing transponder from transmitting data at the same time as an adjacent like device. Similar to previously developed transponders, the control circuit can also be encoded with data pertaining to the biosensing transponder, the patient, and/or other implanted devices within the patient, and can transmit this data to the remote reader when energized. Where a biosensing transponder utilizes optical emitters for illuminating an implant site, or for optically transmitting data to a remote reader, the control circuit can also be configured to control activation of the optical emitters, such as by alternately illuminating a pair of optical emitters by controlling pulsatile discharges of a storage capacitor.

Disclosed embodiments of the biosensing transponder of the present invention include temperature sensors, strain sensors, ultrasonic sensors, pressure sensors, chemical sensors including direct chemical sensors and dye based chemical sensors, magnetic sensors, acoustic wave sensors, ionizing radiation sensors, acceleration sensors, and photosensors including spectrophotometers. However, these embodiments are merely intended to be exemplary of the various implementations that are available, and are not intended to be an exhaustive list.

Sensors having one or more electrodes can be implemented in the present invention for a number of purposes, including for measuring biopotentials, for detecting wear or failure of mechanical prostheses, and for detecting the presence or levels of specific chemicals. When desired, the electrodes can be coated with ion-selective membranes, or can be separated from an external environment by a selectively permeable membrane such as a gas permeable membrane. Typically, sensors having electrodes are positioned within a sealed capsule with one or more of the electrodes extending through the capsule to an external environment. However, the sensor itself can be positioned in the external environment such as by sealing the sensor over an opening in a capsule containing the energy coupler and control circuit.

In other embodiments, the biosensor can be completely positioned within a capsule containing the energy coupler and control circuitry, and sense parameter values from the external environment through the capsule. Examples include biosensing transponders utilizing temperature sensors, strain sensors, ultrasonic sensors, acceleration sensors, ionizing radiation sensors, magnetic sensors, optical sensors and pressure sensors. In the case of biosensing transponders utilizing pressure sensors, the capsule may include a pressure transmissive region or membrane for coupling an external pressure to the pressure sensor, often in conjunction with an incompressible fluid.

Biosensing transponders can also include one or more photosensors for optically detecting physical properties at the implant site. For example, the biosensor may comprise an array of photosensors, such as an imager, for providing an image of the implant site to the remote reader. In such a case, the imager can be positioned within a transparent capsule having an integral lens for focusing an image from the implant site onto the imager. One or more photosensors can also be used in a biosensing transponder for performing optical radiation detection.

Biosensing transponders utilizing photosensors can also include one or more optical emitters for illuminating the implant site with specific wavelengths. For example, red and infrared light emitting diodes (LEDs) can be used for alternately illuminating the implant site to facilitate optical oximetry. Similarly, optical emitters can be used to illuminate chemical sensitive dyes so that the photosensor can detect a change in an optical property of the dyes to thereby detect a physical property of the external environment. The photosensor can be used with optical filters for shielding the photosensor from particular wavelengths, or the photosensor can be embodied in an integrated spectrophotometer.

Thus, the biosensing transponder of the present invention can be configured to detect almost any physical property or parameter value related to an organism, and wirelessly transmit this information to a remote reader in a simple, inexpensive, and non-invasive fashion. The detected physical property may directly relate to a patient's tissue or cells, or may instead be related to any other implant within the patient. Additionally, the biosensing transponder of the present invention can be utilized with other medical devices, including flexible catheters, for facilitating various observations and procedures.

While the principal advantages and features of the invention have been described above, a greater understanding of the invention may be attained by referring to the drawings and the description of the preferred embodiments which follow.

DETAILED DESCRIPTION OF THE PREFERRED EMBODIMENTS

According to the present invention, which relates to an implantable biosensing transponder and methods of use thereof, the biosensing transponder includes a biosensor for sensing one or more physical properties or parameter values related to the organism after the device has been implanted, and a transponder for wirelessly coupling energy to the device from a remote energy source and for wirelessly transmitting data corresponding to the sensed parameter value to a remote reader. The biosensing transponder need not contain any on-board electrical power sources, such as batteries, and is therefore particularly suitable for human implantation as it can remain implanted and provide valuable information related to a patient for an indefinite length of time, and can be accessed in a non-invasive manner after implantation. The absence of an on-board electrical power source also reduces the size of the device and, consequently, the amount of space required for implantation.

By selecting one or more particular types of sensors for inclusion in the device of the present invention, the biosensing transponder can be configured to study or monitor nearly any physical or chemical property related to a patient. As used herein, the phrase "any physical property" or "parameter value" related to a patient or organism shall include, in addition to the physiological parameters of the patient, any information pertaining to other implants in the patient, including living tissue implants, temporary implants such as drug release and organ displacement devices, reconstructive and cosmetic implants, medical prostheses, and other implantable transponders.

Figure 1:
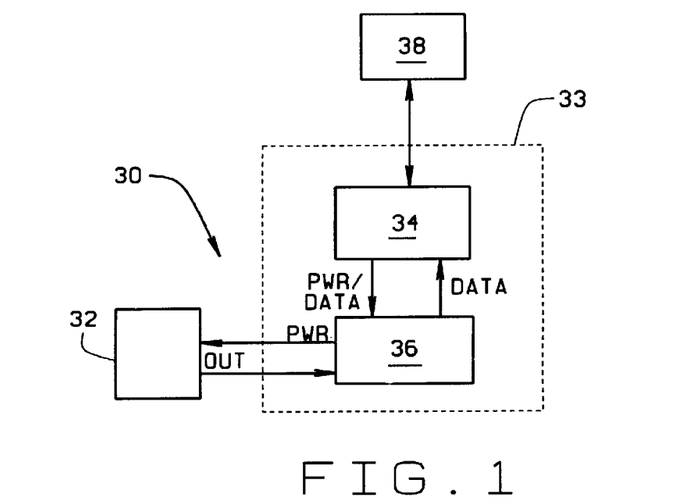
FIG. 1 is a block diagram of the implantable biosensing transponder of the present invention.

As shown in FIG. 1, a biosensing transponder 30 includes a biosensor 32 and a transponder 33 having at least one energy coupler 34 and a control circuit 36. After implantation, energy coupler 34 couples power and any command signals from a remote interrogator or reader 38 to control circuit 36 which, in turn, energizes biosensor 32. Upon being energized, biosensor 32 detects one or more physical properties of its surrounding environment, including optical, chemical, and electrochemical properties, and provides an output signal of the detected physical property to control circuit 36. The control circuit then sends data indicative of the detected physical property to remote reader 38 with energy coupler 34 or with a different energy coupler (not shown). Thus, biosensing transponder 30 need not include any batteries or other sources of electrical power, and can instead be conveniently energized with remote reader 38 after implantation to sense particular parameter values and to wirelessly transmit data indicative of the sensed parameter values to remote reader 38.

As with previously developed transponders, control circuit 36 can also be encoded with identifying data before or after implantation. Such data may relate to the biosensing transducer 30, the organism into which the device is implanted, or both. The identifying data may also be a unique tag for accessing data stored in a remote data bank, such as a personal computer or a memory device in remote reader 38. Hence, even after implantation of biosensing transponder 30, identifying data can be conveniently retrieved from control circuit 36 in a non-invasive manner, as can data corresponding to sensed parameter values. In the preferred embodiments of the present invention, any identifying data encoded in control circuit 36 is transmitted to remote reader 38 by energy coupler 34 just prior to transmitting the data that corresponds to the sensed parameter value.

Typically, energy coupler 34 is an inductive circuit for energizing transponder 33 with a hand held electromagnetic reader, and for electromagnetically transmitting data from control circuit 36 to the hand held reader. The hand held electromagnetic reader emits a low frequency magnetic field to activate the passive biosensing transponder and thereby causes it to transmit data to the reader. However, in some applications, electromagnetic coupling may be impractical, such as where generation of the required magnetic field will interfere with external equipment. In such an event, alternatives to electromagnetic coupling may be necessary.

According to the present invention, energy may instead be provided to control circuit 36 in the form of ultrasonic vibrations. As is well known, piezoelectric transducers are bidirectional and can be driven electrically by applying an AC signal to two electrodes on opposite surfaces of a piezoelectric slab to result in a mechanical vibration having the same frequency as the applied signal. In this manner, biosensing transponder 30 can utilize a piezoelectric transducer to transmit data from control circuit 36 to a remote ultrasonic reader. Conversely, the piezoelectric slab can be mechanically vibrated to result in a generation of electric potentials on the two electrodes. Thus, a single piezoelectric element can be utilized to both couple power into the biosensing transponder and to transmit data therefrom. Other types of ultrasonic transducers can also be used as apparent to those skilled in the art.

Ultrasonic coupling is particularly advantageous as conventional medical ultrasound instrumentation can be used to energize and retrieve data from biosensing transponder 30. Command signals can also be ultrasonically transmitted to control circuit 36 by modulating the incident ultrasonic energy such as by periodically short-circuiting the piezoelectric transducer (thus modulating its acoustic impedance), periodically driving the piezoelectric transducer electrically in a pulsatile or other manner to emit a desired signal, or by other methods apparent to those skilled in the art. Suitable piezoelectric materials include lead zirconate titanate (PZT), quartz, polyvinylidene fluoride, and zinc oxide (ZnO). ZnO is a common piezoelectric material used in microfabrication and can be sputter deposited on a substrate as a polycrystalline thin film with its c-axis, along which piezoelectricity is strongest, perpendicular to the surface of the substrate.

As another alternative to electromagnetic coupling, high-efficiency photoelectric devices, i.e., solar cells, can be used as energy coupler 34 so that power can be optically transmitted to transponder 33, such as by using red and infrared wavelengths that pass relatively well through tissues. The solar cells can collect sufficient energy from an external infrared emitter to energize the low-power CMOS control circuit 36 used in the preferred embodiments. Command signals can be transmitted to transponder 33 by modulating the incident optical energy. Similarly, one or more on-board red or infrared LEDs can be used for transmitting data from control circuit 36 to an external optical reader in the form of encoded pulses of light.

It should be understood that while ultrasonic and optical coupling have been described as alternatives to electromagnetic coupling for the implantable biosensing transponder of the present invention, these coupling techniques are equally suitable for coupling energy to and/or from implantable transponders which are used without biosensors. For example, ultrasonic and optical coupling can be used with a previously designed transponder for energizing and providing command signals to the transponder, and for transmitting identifying data, including unique tags, from the transponder to a remote reader. Moreover, transponder 33 can include more than one energy coupler 34, particularly where it is advantageous to energize the biosensing transponder with one form of energy, and transmit data using another. Where desirable, a third energy coupler can also be used to receive control commands from an external source using either the same or different forms of energy as those used for energizing the transponder and transmitting data therefrom.

Figure 2:
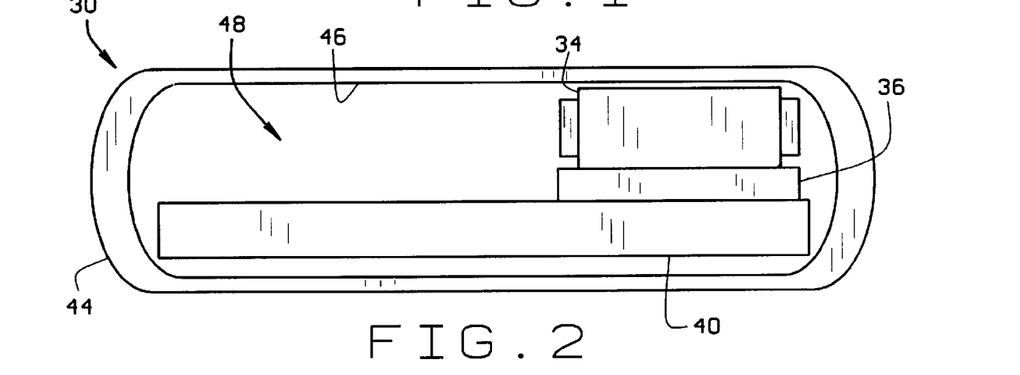
FIG. 2 illustrates a typical physical implementation of the biosensing transponder of the present invention.

The physical implementation of an implantable biosensing transponder according to a first embodiment of the present invention is illustrated in FIG. 2. A substrate 40 is provided for supporting energy coupler 34, control circuit 36 which is embodied in an integrated circuit, and one or more biosensors (not shown) for sensing the value of predetermined parameters after implantation of the biosensing transponder 30. If substrate 40 is formed from silicon or another semiconductor material, various types of biosensors and/or control circuit 36 can be integrated therein. If such integration is not desired, the substrate can still be used as an electrical interconnection between control circuit 36, one or more biosensors, and any additional components within the transponder as apparent to those skilled in the art of hybrid substrate fabrication. A capsule 44 protects energy coupler 34, control circuit 36, and any biosensors positioned therein from an external environment, and is preferably formed from glass. As shown in FIG. 2, a substantial amount of space 48 is reserved within capsule 44 for accommodating one or more biosensors. Although capsule 44 is illustrated as being generally cylindrical, it should be understood that it can be virtually any shape necessary for a given application or manufacture.

Where a piezoelectric transducer is utilized as energy coupler 34, either with or without a biosensor, the transducer can be bonded to an interior wall 46 of capsule 44 to detect ultrasonic energy impinging upon capsule 44. Alternatively, the piezoelectric transducer can be placed anywhere within capsule 44, and an appropriate coupling material, such as a nonconductive and incompressible liquid like silicone oil, can be contained within the capsule to efficiently couple ultrasonic energy impinging upon capsule 44 to the piezoelectric transducer.

Although only a limited number of sensors will be described herein for implementation in the implantable biosensing transponder of the present invention, it should be understood that a virtually endless number of sensors can be utilized, limited only by the size of a particular sensor. With further advancements in technology, including advancements in micromanufacturing as well as the advent of new and alternative sensors that are smaller than those presently available, even a greater number of sensors will be available for use in implantable biosensing transponders. Moreover, depending upon the physical characteristics of a particular implantation site, capsule 44 can be enlarged to thereby accommodate larger sensors.

It should be noted that multiple sensors of various types can be utilized in a single biosensing transponder. The control circuitry can be designed to either sequentially activate and transmit information from the multiple sensors or to individually activate each sensor upon receiving an appropriate external control signal. The design of such circuitry can be easily achieved as apparent to those skilled in the art of electronic circuit design.

A temperature sensor is one of the many types of sensors that can be utilized with the implantable biosensing transponder of the present invention. Because biosensing transponder 30 will reach ambient temperature shortly after implantation, a temperature sensor can be provided within capsule 44 to measure an internal temperature that is representative of a temperature of the environment external to capsule 44. Such a temperature sensing transponder is useful, for example, for monitoring transplanted tissue, such as flaps or organs, as an assessment of blood flow. This is a low-power function, and can be carried out using approximately the same amount of energy as used by previously designed transponders for transmitting identifying data. Where temperature sensors are utilized which require post-fabrication calibration, calibration factors can be stored in control circuit 36, or in an external device for access upon remotely retrieving identifying data from control circuit 36.

Examples of suitable silicon based temperature sensors include diode based temperature sensors, band-gap based temperature sensors including those utilizing proportional to absolute temperature (PTAT) circuits, and other silicon based temperature sensors that utilize various forms of digital outputs. Non-silicon-based devices, such as thermistors, platinum resistive temperature sensors, thermocouples, etc., can also be implemented in an implantable biosensing transponder. Where a solid-state temperature sensor is utilized, it can be embodied in an integrated circuit with control circuit 36, and/or integrated into a silicon substrate.

A magnetic sensor, such as a Hall sensor, can also be used as a biosensor according to another embodiment of the present invention. The magnetic sensor can be embodied in an integrated circuit with control circuit 36 by using conventional bipolar or MOS components, and/or integrated into a silicon substrate. A biosensing transponder configured in this manner can be used, for example, to determine the distance and/or angle between the biosensing transponder and a prosthesis having a magnet affixed thereto.

In another embodiment of the present invention, an accelerometer can be utilized as a biosensor for detecting or monitoring acceleration of tissues, for example. As is well known, micromachined accelerometers are commercially available and can be easily implemented in a biosensing transponder. Such a biosensing transponder can then be used for monitoring accelerations of tissue such as the walls of chambers of the heart by attaching the biosensing transponder thereto.

In still another embodiment of the present invention, a direct ionizing radiation detector can be used as a biosensor. Direct ionizing radiation detectors exploit the fact that ionizing radiation entering a semiconductor will cause multiple electron-hole pairs to be generated, resulting in a directly detectable electrical current for each particle. The direct detector may be either a bulk region of semiconductor, a conventional pn diode, or a more complex structure such as a p-i-n diode. In this embodiment of the invention, well-known measures can be taken to make the rest of the transponder circuitry less sensitive to ionizing radiation such as by shielding sensitive areas with an electron-dense metal such as gold, by using radiation-tolerant circuit design techniques, and/or by using radiation tolerant device fabrication processes such as silicon-on-insulator processes. Thus, a separate region of the chip containing the transponder control circuitry can be used as the detector where that region does not have shielding or other measures to reduce its radiation sensitivity. Alternatively, a separate detector chip can be provided. A biosensing transponder configured in this manner is particularly suitable for monitoring therapeutic or unintentional doses of ionizing radiation.

Another type of sensor that can be utilized with the present invention is a dye-based chemical sensor. As is well-known in the art, there are many techniques for using organic and inorganic dyes as chemical sensing elements. These dyes have one or more optical properties that change when the dyes are exposed to particular chemicals. Upon excitation by a suitable light source, such a dye emits a fluorescence at a particular wavelength, or with a fluorescence intensity, that is proportional or related to a specific parameter, such as pH, voltage, or ion concentration. Some examples of chemical sensitive dyes, by no means exhaustive, include a bicarbonate buffer emulsion in silicone for sensing $CO_2$, hydroxypyrene trisulfonate in cellulose for sensing pH levels, and decacyclene in silicone for sensing $O_2$.

Figure 3:
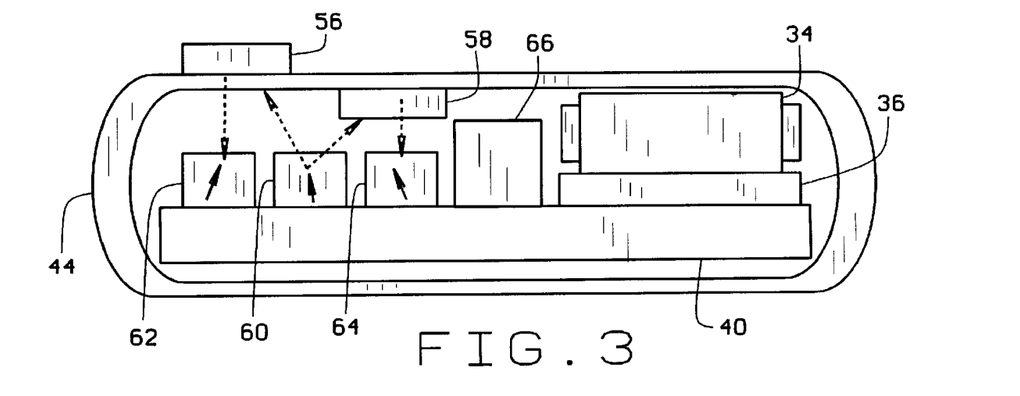
FIG. 3 illustrates a biosensing transponder for optical interrogation of chemical sensitive dyes.

An example of a biosensing transponder that uses a dye-based chemical sensor is illustrated in FIG. 3. A dye 56 is positioned on an exterior portion of capsule 44, thereby exposing dye 56 to the external environment, and may be implanted in contact with tissue, blood, cerebrospinal fluid, etc. Dye 58, which is of a same type as dye 56, is positioned within capsule 44. Capsule 44 is constructed from transparent glass so that optical interrogation of dye 56 can be accomplished from within capsule 44.

An optical emitter 60 is provided for illuminating dyes 56 and 58 to excite the dyes and thereby cause them to emit their fluorescence, and photosensors 62 and 64 are provided for detecting the optical properties of dyes 56 and 58, respectively, during or immediately after illumination. Alternatively, the biosensing transponder can utilize multiple spectrophotometers for detecting the optical properties of dyes 56 and 58, or a single spectrophotometer if the biosensing transponder uses only one chemical sensitive dye. While dye 56 is provided on an exterior portion of capsule 44 in contact with the external environment, dye 58 is positioned within capsule 44 to thereby isolate it from the external ambient. Given that dyes 56 and 58 are of the same type, and should therefore have the same optical properties, differential sensing is accomplished by photosensors 60 and 62, in conjunction with control circuit 36, to provide more reliable measurements and to compensate for any drifts in the dye properties over time.

To measure fluorescence at particular wavelengths, optical band-pass filters are used in combination with photosensors 62 and 64 for allowing only fluorescent light to pass through the filters and reach photosensor 62 and 64 while shielding the photosensors from excitation and extraneous light. Such filters are readily fabricated by depositing subsequent layers of thin films, such as metallic oxides, on suitable optically transparent substrates such as glass, or at predetermined locations on the interior wall of capsule 44, or directly on top of the photosensor structures.

The optical wavelength(s) required to excite the dyes are determined by the particular types of dyes that are used. Example of suitable emitters for use in an implantable biosensing transponder include blue light emitting diodes, such as SiC or GaN, as well as green, yellow, orange, red, and infrared LEDs and miniature incandescent bulbs. Low power operation of these optical emitters is achievable by operating them in a pulsed manner, i.e., only energizing them when a measurement is desired. Control circuit 36 can control the pulsing of the optical emitters.

As shown in FIG. 3, a storage capacitor 66 is utilized for providing pulses of electrical energy to optical emitter 60 at power levels that are greater than the continuous power received by energy coupler 34. By storing energy received from control circuit 36 in capacitor 66, or alternatively in an inductor, optical emitter 60 can be indirectly energized by control circuit 36 through a pulsatile discharge of capacitor 66. Of course, where the continuous power received by energy coupler 34 from a remote reader is at a sufficient power level to energize optical emitter 60, capacitor 66 can be omitted.

As an alternative to the embodiment illustrated in FIG. 3, optical emitter 60 can be eliminated, and dyes 56 and 58 can be illuminated with an external optical emitter at wavelengths, such as those in the infrared range, that can readily penetrate the tissues of the organism into which the biosensing transponder is implanted. Thus, illumination can be provided from a light source external to the organism in which the biosensing transponder is implanted.

There are numerous techniques available for utilizing organic and inorganic dyes to sense chemical properties, any of which can be implemented in an implantable biosensing transponder without departing from the scope of the present invention. For example, it is well-known that if chemical sensitive dyes are illuminated in a pulsed fashion, the resulting pulse of fluorescent light will decay exponentially over time as a function of the chemical phenomenon of interest. Control circuit 36 can be adapted to cause photosensors 62 and 64 to measure the fluorescent signals at a fixed time after the illumination pulse to obtain a measure of the chemical phenomenon of interest.

Similar to the previously described embodiment that utilizes photosensors for optical interrogation of chemical sensitive dyes, photosensors can also be used in a biosensing transponder for direct optical sensing of the implantation environment, either for directly obtaining optical information, such as the color of a particular organ, or for performing an optical technique such as oximetry to determine the oxygen saturation of hemoglobin in blood based on the absorption or backscattering of optical energy. In the latter case, the transponder is positioned, for example, within a pulsatile tissue bed for performing pulse oximetry, and the relative quantity of oxygen carried in arterial blood is determined by optically measuring color variations of deoxyhemoglobin and oxyhemoglobin.

Figure 4:
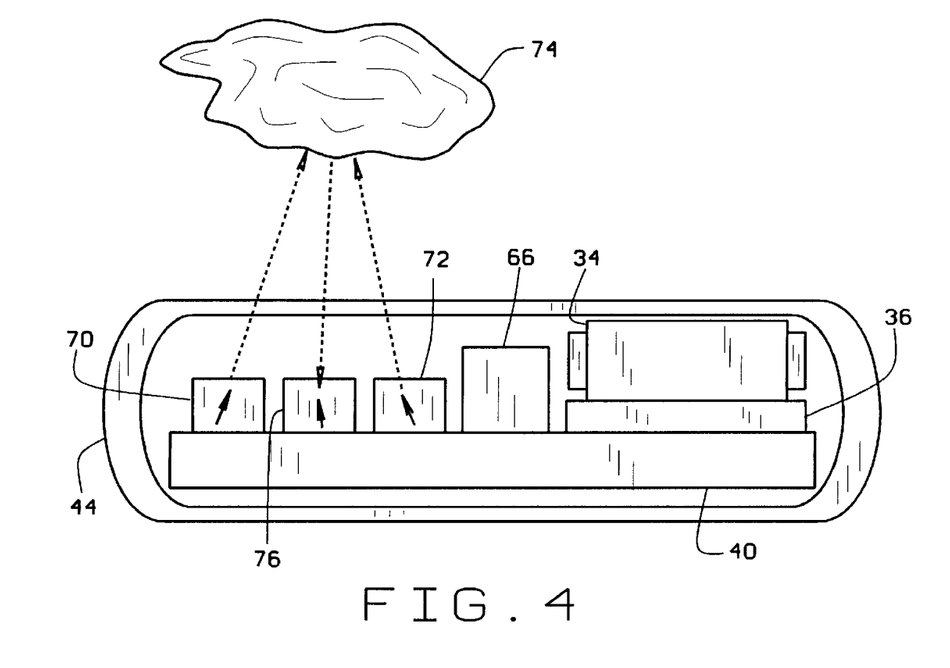
FIG. 4 illustrates a biosensing transponder for direct optical interrogation of an external environment.

An implantable biosensing transponder configured for performing optical oximetry is illustrated in FIG. 4. Optical emitters 70 and 72 are provided for illuminating a tissue 74 located in the external environment. Optical emitter 70 is a visible red LED for illuminating tissue 74 at a wavelength of 660 nanometers at which there is a great difference between the optical absorptions of the two forms of hemoglobin. Optical emitter 72 is an infrared LED for illuminating tissue 74 at a wavelength of approximately 800 nanometers at which the optical absorptions of the two forms of hemoglobin are nearly independent of their oxygenation states.

A photosensor 76 is positioned between optical emitters 70 and 72, and is provided for measuring optical energy that is backscattered by the pulsatile tissue bed (photoplethysmogram) 74 upon illumination by the optical emitters. By mathematically dividing the amplitudes of the two backscattered light signals detected by photosensor 76, a function performed by control circuit 36, the signals are normalized for offsets caused by incident light intensity, degree of vascularity, etc. to thereby provide a measure of oxygen saturation that is independent of these undesirable effects.

In operation, optical emitters 70 and 72 are alternately illuminated in brief pulses using energy stored in storage capacitor 66. Photosensor 76 detects some fraction of the emitted energy, i.e., backscattered optical energy, and provides this information to control circuit 36 for computing the oxygen saturation level and for transmitting data indicative of the oxygen saturation level to a remote reader via energy coupler 34. Similarly, oximetry in the brain can also be performed using cytochrome aa3 (the terminal member of the respiratory electron transport chain), the optical absorption of which changes with its degree of oxygenation.

Photosensors can also be utilized in the implantable biosensing transponder of the present invention for directly obtaining optical properties of the external environment. For example, assessment of the degree of fibrosis around an implant, such as a breast implant, can be made by measuring the optical properties of the surrounding tissue. This is analogous to inspection of tissues by eye and the data corresponding to the measured optical properties can be transmitted to a remote device for display of optical properties in the visible range on a computer monitor, for example. Photosensors can also be used as scintillator or phosphor-based ionizing radiation detectors for monitoring therapeutic or unintentional doses of ionizing radiation. Scintillators or phosphor-based detectors make use of the fact that radiation entering certain materials causes photons to be emitted. The level of light generated by the emitted photons is directly proportional to the radiation level. These photons can then be detected using conventional photosensors, such as photodiodes or phototransistors, which could be integrated with the transponder control circuitry and/or the substrate using the well-known measures discussed above with respect to the direct ionizing radiation sensor embodiment for making the rest of the transponder circuitry less sensitive to ionizing radiation.

Figure 5:
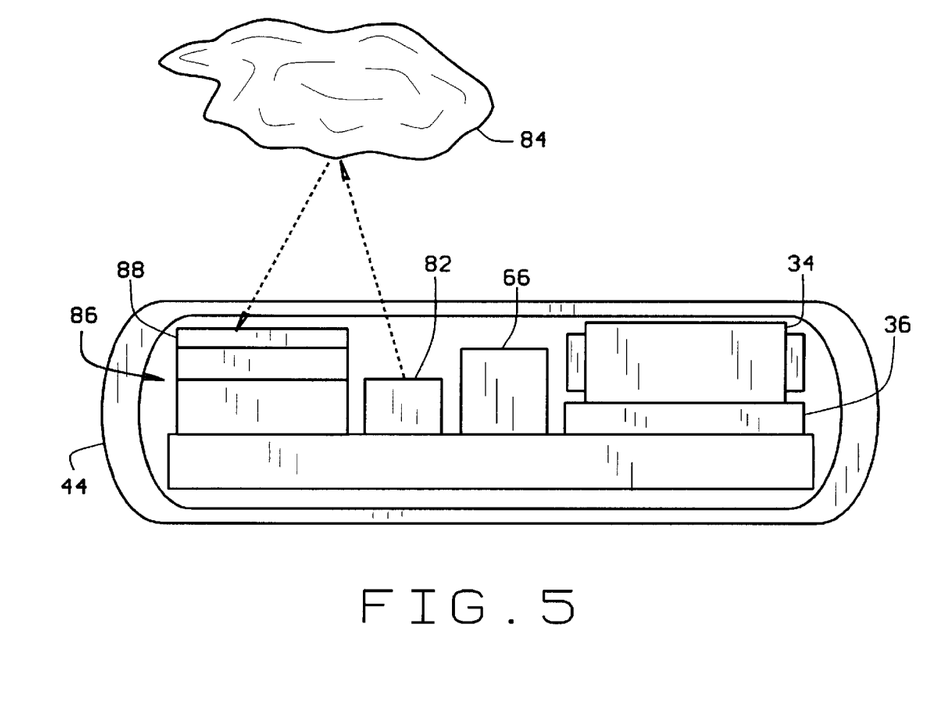
FIG. 5 illustrates a biosensing transponder for direct optical interrogation of the external environment with an integrated spectrophotometer.

FIG. 5 illustrates another embodiment of the implantable biosensing transponder for directly obtaining optical information related to the external environment. An optical emitter 82 illuminates a tissue 84 in the external environment each time the optical emitter receives a pulse of electrical energy from storage capacitor 66. A spectrophotometer 86 measures the optical energy returning from the illuminated tissue as a function of wavelength, and permits accurate analysis of the color of tissue 84.

More specifically, optical energy reflected by tissue 84 is intercepted by the spectrophotometer grating 88, which consists of an opaque pattern of chromium, for example, on a substrate that is transparent to the wavelengths of interest. Grating 88 can be designed to correspond to one or more specific optical spectra, such as wavelengths corresponding to particular molecules, or can be designed as the equivalent of a prism for splitting the reflected optical energy into "bins" corresponding to wavelength ranges. In either case, reflected optical energy that penetrates grating 88 impinges on a photosensor array which, in turn, provides spectral information to control circuit 36. Alternatively, optical emitter 82 can be eliminated, and illumination provided externally at wavelengths that can readily penetrate tissues.

By using the implantable biosensing transponder illustrated in FIG. 5, a wide variety of specific components can be detected provided that their absorption spectra are sufficiently distinct from those of background constituents. For example, the spectrum of optical energy transmitted through a fluid, such as cerebrospinal fluid, can be analyzed to determine turbidity and the relative concentrations of constituents such as proteins and sugars. Similarly, optical assessments of tissue status can be made, such as assessing levels of perfusion and levels of fibrosis. Although such assessments are ordinarily made by simple visual observation, with the implantable biosensing transponder of FIG. 5, such observations can be made more accurately and in locations within the body that would otherwise require further invasive procedures.

Figure 6:
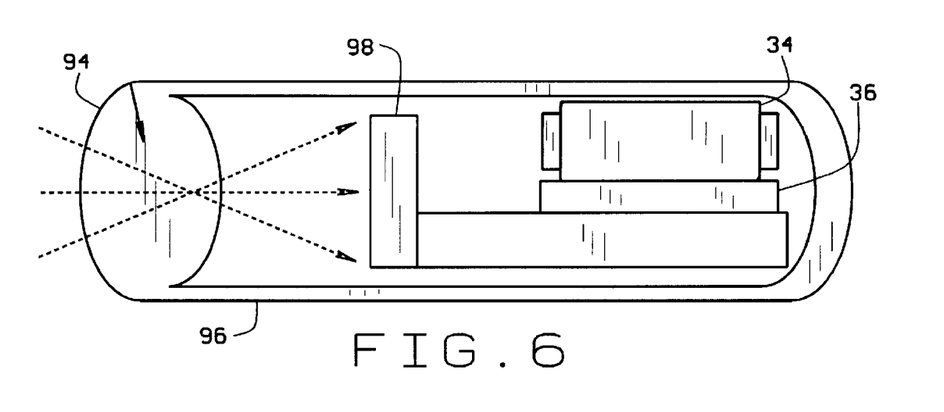
FIG. 6 illustrates a biosensing transponder for detecting images from the external environment.

As shown in FIG. 6, optical imaging functions can also be integrated into the implantable biosensing transponder of the present invention. The CMOS process that is used to fabricate the control circuitry of the preferred embodiments can also be used to fabricate a two dimensional array of photosensors, i.e., an imager. A lens 94 is formed on one end of a capsule 96 for focusing an image of external tissues onto an imager 98 positioned within capsule 96. Preferably, lens 94 and capsule 96 are integrally formed from glass, although lens 94 can also be formed from other materials having suitable focusing properties. Lens 94 can also be separately supplied as a micromachined Fresnel Zone Plate.

Imager 98 is preferably either a charge-coupled device (CCD) or a lower cost metal-oxide-photodiode-type imager implemented in CMOS, both of which are capable of sensing wavelengths that readily penetrate tissue, including infrared wavelengths. Although imager 98 is fixed-focus, appropriate design can yield the desired depth of field. As apparent to those of skill in the art, the usefulness of this embodiment is clearly subject to effective physical placement of the device.

After implantation of the biosensing transponder illustrated in FIG. 6, the external environment can be externally illuminated with an optical source operating at a wavelength that readily penetrates tissue. Optical energy reflected from tissue in the external environment will then be focused onto imager 98 by lens 94. As a result, imager 98 provides signals to control circuit 36 which, in turn, transmits data corresponding to the detected image to a remote reader via energy coupler 34. Alternatively, one or more optical emitters can be provided within capsule 96 as described above. As should be apparent, there are several embodiments of biosensors which utilize optical energy to measure a parameter, either directly or indirectly. These are all considered to be optical interrogators.

Figure 7:
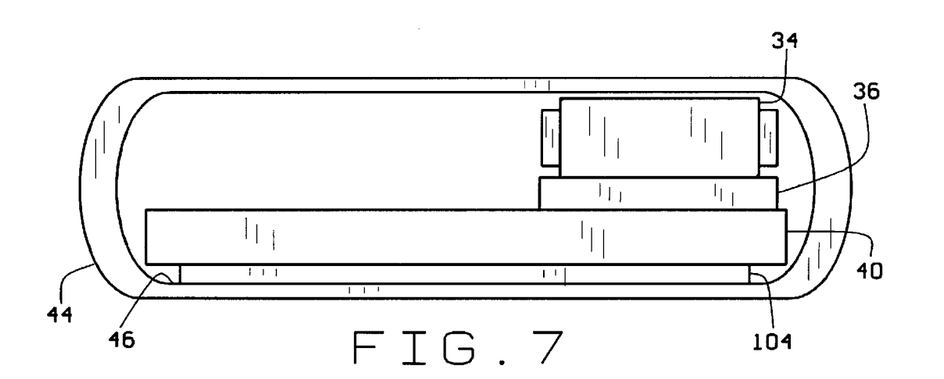
FIG. 7 illustrates a biosensing transponder for detecting strain forces.

Yet another example of a sensor that can be implemented in the implantable biosensing transponder of the present invention is a strain sensor. Such a device enables remote sensing and retrieval of information relating to the strain or force acting on the implanted device and, if the device is mechanically coupled to another device, the strain or force acting thereon. Similarly, a strain sensing transponder can be cemented to a bone, or in the mechanical junction between a bone and a prothesis, for providing strain information related to the bone and/or junction. This strain sensing capability can be extremely valuable where feedback regarding loads, torques, etc. is clinically necessary or beneficial. As illustrated in FIG. 7, a strain sensitive layer 104 is bonded to interior wall 46 of capsule 44 and provides strain information to control circuit 36. Suitable strain sensors for this embodiment include resistive and piezoresistive strain sensors, as well as metal and semiconductor strain gauges. As an alternative to bonding strain sensitive layer 104 to capsule 44, the layer may be fabricated directly onto substrate 40 using well-known semiconductor and thin-film strain gauge techniques.

Figure 8:
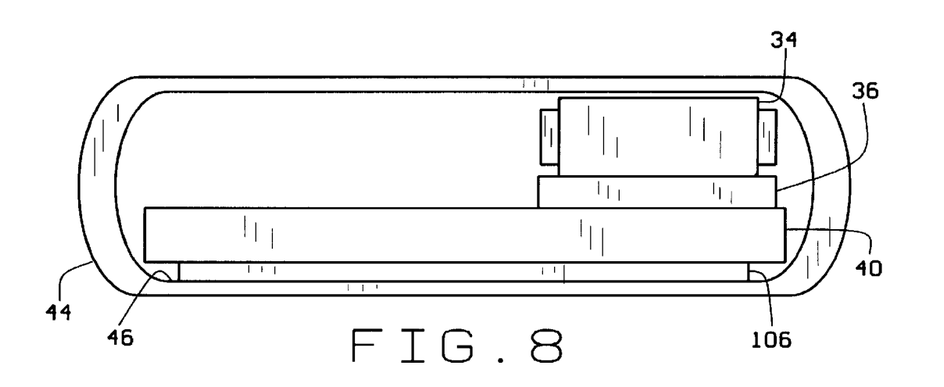
FIG. 8 illustrates a biosensing transponder for performing doppler velocity measurements.

FIG. 8 illustrates another embodiment of the present invention where a piezoelectric element 106 is implemented in an implantable biosensing transponder to perform doppler velocity measurements to determine the velocity and direction of the flow of a fluid, such as blood. Piezoelectric transducer 106 can be used as an ultrasound emitter to irradiate, for example, blood flowing in a vessel. At the same time, the piezoelectric transducer of a like device is used as an ultrasound collector to receive the emitted waves, where the frequency of the received waves are shifted in proportion to the velocity of the blood. Thus, if the cross-sectional area of the vessel is known, the flow of blood can be determined. As should be apparent, successful performance of this measurement technique requires proper placement of the ultrasound emitter and detector, such as by proper placement of these devices within a vascular graft. Where the ultrasound emitter and detector are to be embodied within a single capsule, they must be positioned so that one is somewhat downstream relative to the other with respect to the flow of fluid to be measured. The device of FIG. 8 can, similarly, be used in conjunction with a like device to "bounce" ultrasonic energy off a moving surface, such as a heart, to dynamically determine its velocity.

In another embodiment of the present invention, the piezoelectric element 106 of the biosensing transponder illustrated in FIG. 8 can be replaced with an acoustic wave sensor which, itself, is typically comprised of piezoelectric transducers generally disposed on opposite sides of a membrane. One of the piezoelectric transducers is used to launch an acoustic wave along the membrane, and the other is used to receive the launched acoustic wave. In this embodiment of the present invention, an opening is provided in the capsule 44 so as to expose the membrane of the acoustic wave sensor to the external environment. Anodic bonding, adhesives, or other techniques can be used to form a hermetic seal around the opening and between the capsule and the peripheral support of the acoustic wave sensor. The membrane of the acoustic wave sensor can be coated with a chemically-sensitive layer, i.e., a polymer layer containing a receptor molecule such as a monoclonal antibody, selected for sensing the presence of a particular compound. If present at the same location in the organism as the biosensing transponder, the particular compound will bind with the chemically-sensitive layer to thereby change the mass of the membrane of the acoustic wave sensor. As a result, the propagation delay of the acoustic wave along the membrane is changed, where the amount of change in the propagation delay is proportional to the mass of the sensed compound which bound to the chemically-sensitive layer.

Another benefit of this embodiment is that by appropriately controlling activation of the ultrasonic energy generated by the acoustic wave sensor, fluid can be actively circulated past the sensitive membrane in order to greatly speed up binding kinetics relative to those possible by simple diffusion. The acoustic wave sensor can also be used in certain applications for mixing and moving fluids and/or particles without applying a chemically-sensitive layer to the membrane of the acoustic wave sensor. In each of these various embodiments, the acoustic wave sensor preferably has the piezoelectric transducers positioned on the same side of the membrane and sealed within the interior volume of the transponder capsule to eliminate a need for specially insulating the piezoelectric transducers from the external environment.

Figure 9:
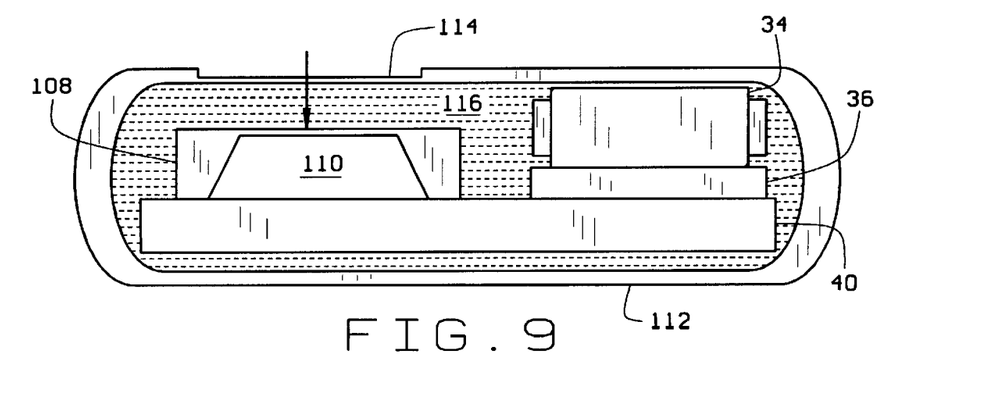
FIG. 9 illustrates a biosensing transponder for detecting pressures.

FIG. 9 illustrates still another embodiment of the present invention where a pressure sensor 108 is implemented in an implantable biosensing transponder to allow remote sensing and retrieval of static and dynamic pressure information. Pressure sensor 108 is bonded, i.e., anodically bonded or glued, to substrate 40, and includes a sealed reference cavity 110 containing a vacuum or gas. Capsule 112 has a pressure transmissive region 114, and is filled with a nonconductive and incompressible fluid 116 for coupling an external pressure exerted on pressure transmissive region 114 to pressure sensor 108. Pressure sensor 108 provides a signal to control circuit 36, indicative of the pressure exerted on reference cavity 110 by incompressible fluid 116, for transmission of this information to a remote reader. Pressure transmissive region 114 may be formed by any means appropriate for the particular capsule material utilized, provided that the hermeticity of capsule 112 is not destroyed. For example, glass may be selectively ground mechanically, or chemically etched using hydrofluoric acid. Alternatively, a thin membrane can be sealed over a hole in capsule 112, such as an opening in one end of a cylindrical capsule, for coupling pressure into the capsule interior. Suitable pressure sensors include micromachined low-power solid-state pressure sensors.

Figure 10:
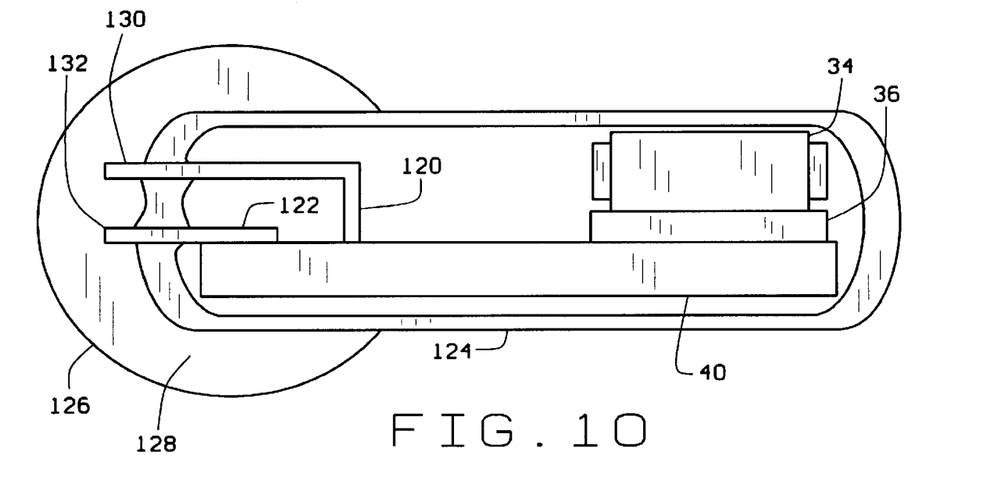
FIG. 10 illustrates a biosensing transponder having electrodes exposed to the external environment.
Figure 11:
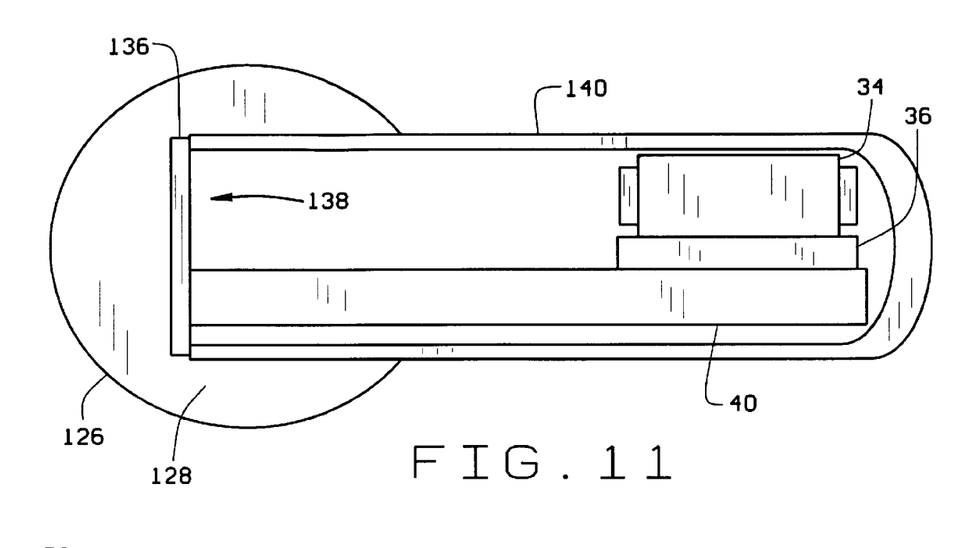
FIG. 11 illustrates a biosensing transponder with the biosensor directly exposed to the external environment.

FIGS. 10 and 11 illustrate additional configurations of the implantable biosensing transponder of the present invention where at least a portion of the biosensor is directly exposed to the external environment. These configurations are particularly suitable for biosensors that monitor the condition of other artificial devices, such as prostheses, positioned in the external environment, as well as for direct chemical sensors that must be in chemical contact with the substance to be sensed.

As shown in FIGS. 10 and 11, gas- or ion-permeable or ion-selective membranes 126 can also be used to form regions 128 around the biosensors so that the regions 128 achieve equilibrium with dissolved or free gases or ions, depending upon the implantation site and the particular parameter value to be measured. Gas- or ion-permeable or ion-selective membranes 126 can also be incorporated into the capsule construction with the biosensor positioned completely therein. In either case, the membranes separate the biosensor from the external environment with the exception of desired gases or ions that can penetrate the membrane.

As shown in FIG. 10, two electrodes 120 and 122 are electrically connected to substrate 40 and have electrode tips 130 and 132, respectively, that protrude through a portion of capsule 124 to contact the external environment. The electrodes 120 and 122 are held in place while capsule 124 is sealed in order to form hermetic feedthroughs. The electrode tips 130 and 132 can be coated with ion-selective or protective membranes for facilitating electrochemical measurements such as impedance spectroscopy, voltammetry, amperometry, etc. By using a variety of electrochemical techniques and a variety of membrane and electrode materials, a multitude of chemical sensors can be implemented, some of which may require one or more electrodes in addition to electrodes 120 and 122.

The implementation of FIG. 10 is also particularly suitable for measuring biopotentials, where electrodes 120 and 122 are connected internally to high impedance amplifier circuitry to enable measurement of very small differential voltages, or biopotentials, between the electrodes which may, depending on the location of the device, represent the activity of cardiac tissue, skeletal or smooth muscle, or neural tissue. In this application, the membrane 126 might not be used. Example electrode materials for measuring biopotentials include platinide metals (platinum, iridium, etc.) and gold. Depending upon the recording site to be measured, electrodes 120 and 122 may need to be spaced further apart from their positions illustrated in FIG. 10, such as on opposite ends of capsule 124. Biopotential signals are typically recorded with a reference electrode located away from the recording site.

Since biopotentials are typically measured without penetrating cell membranes with probes, the detected voltages tend to be extremely small, on the order of 100 microvolts to 1 millivolt. Thus, low-noise differential amplifiers with relatively high gains are often required, and may be positioned on substrate 40, or integrated with control circuit 36 or in a silicon substrate. Differential amplifiers help reject interference signals such as radio transmissions and unintentional electromagnetic radiation from computers and other electronic devices, which generally appear equally across both electrodes. Conventional analog or analog switched capacitor filters can also be used after preamplification to further reduce noise pickup.

FIG. 11 illustrates an alternative configuration to the hermetic feedthroughs of FIG. 10. As with the embodiment in FIG. 10, membrane 126 may not be needed and, in some instances, may be eliminated. In this embodiment, a biosensor or biosensor chip 136, which may contain electrodes and/or multiple biosensors, is sealed to an opening 138 in one end of a cylindrical capsule 140. Any suitable technique can be used for sealing the biosensor chip 136 including adhesives, frits, or anodic bonding.

Suitable biosensors for implementation in the embodiment of FIG. 11 include passive chemical sensors such as chemiresistors, where a resistance between two electrical contacts changes upon exposure to a particular chemical. Chemicapacitors can also be used, where the dielectric constant, i.e., capacitance, of a sensitive layer is measured as an indication of relative humidity or the presence of a gas. An example of a suitable chemicapacitor is polyphenylacetylene (PPA), a polymer that can be spun from a benzene solution and is sensitive to CO, $CO_2$, $N_2$, and $CH_4$. The capacitance of the sensitive layer can be measured by any of the techniques well-known in the art.

Ion-sensitive FETs, including ISFETs and CHEMFETs, can also be used in the embodiment of FIG. 11. In the case of ISFETs, the gate insulator is directly exposed to the ionic medium so that the drain current is modulated by ion concentration. By coating the gate region with an ion-selective membrane, CHEMFETs are created which are sensitive to certain ions. Specific compounds can be sensed by using the high specificity of biological molecules such as enzymes and antibodies, which can be incorporated into the gate region of a CHEMFET. Other examples of suitable biosensors include: acoustic wave sensors; electrochemical pH sensors; and ion-sensitive field effect devices that are capable of measuring ion concentrations, dissolved gases, and pharmaceutical concentrations.

As stated above, the configurations illustrated in FIGS. 10 and 11 and similar configurations thereto are also particularly suitable for biosensors that monitor the condition of other artificial devices. One or more electrodes of a biosensor can be electrically connected to an implantable prosthesis to detect mechanical breakdowns or failures with the prosthesis. For example, "tripwires" can electrically connect biosensor electrodes to the frame of a metallic heart valve in order to detect cracking of the valve, hopefully in advance of a complete failure. For example, the wires can be attached to the frame members of a Shiley-type heart valve to detect cracking. Since two arms of the valve frame must crack before failure (and near instant death) occurs, and since the time between cracking of the first side of the frame and the second side is approximately six months, the biosensing transponder can be monitored periodically, such as every three months, to provide an early detection of an impending failure of the heart valve.

Similarly, detection of early leakage of contents from a breast implant, indicating that a frank rupture is likely, could stimulate early intervention to prevent tissue damage and allow replacement of the breast implant in an elective, convenient time frame for the patient. In the case of an implant containing a conductive fluid, a biosensing transponder can be positioned within the implant and have one of its electrodes exposed to the conductive fluid, while another electrode is electrically coupled to the external surface of the implant such as by an insulated wire. Assuming the encapsulation of the implant is electrically insulating, the integrity of the encapsulation can be tested by measuring the impedance between the two electrodes. If the implant is intact, very little or no current will flow between the internal electrode and the wire coupled to the external surface of the implant. Once the encapsulation begins to leak, a lower-impedance current path between the two electrodes will be readily detectable.

Alternatively, a biosensing transponder containing an ultrasonic transducer, such as a piezoelectric element, can be attached to the mechanical prothesis for measuring the resonance frequency of the prothesis to provide an early detection of a mechanical failure. Similarly, two separate biosensing transponders containing ultrasonic transducers can be attached to opposite sides of the mechanical prothesis, using one to emit and the other to receive pulses of ultrasonic power, to detect fractures in the prothesis in a manner similar to that immediately described above.

The electrodes of a biosensing transponder can also be connected to a wire embedded in the surface of an artificial joint that is subject to wear, including joints constructed from polyethylene. After a certain amount of wear, the embedded wire will become exposed and subject to physical damage or deformation. By inducing a current through the embedded wire, changes in the resistance of the wire as a result of physical damage or deformation can be detected. Preferably, the current is induced in pulses so as to minimize power requirements. In this embodiment of the invention, the conductor of the embedded wire is preferably a material that is equally or more susceptible to wear than the prothesis in question so that once the predetermined wear threshold of the prothesis has been reached, the wire will quickly become damaged or deformed and result in a detectable change in its resistance.

Alternatively, a predetermined wear threshold can be determined for a mechanical prothesis by modifying the biosensing transponder illustrated in FIG. 10 such that only one of the electrodes 120 and 122 extends through the capsule 124 to the external environment. With a biosensing transponder configured in this manner, the transponder can be used to detect the predetermined wear threshold in a mechanical prothesis that has an insulated wire embedded therein. One end of the wire is connected to the biosensor electrode that is sealed within the biosensing transponder capsule and isolated from the external environment, while the entire length and other end of the wire is insulated. A small signal, such as a 100 mV peak-to-peak waveform, can then be applied across the two electrodes, and the resulting capacitive current flowing from one electrode to the other can be monitored such as with a transresistance-type amplifier contained within the biosensing transponder. The amount of capacitive current induced will be proportional to the amount of surface area of the insulated wire that is exposed to fluids between the prosthesis and the electrode extending through the capsule. As the mechanical prothesis wears, the AC current will increase as more of the insulated wire is exposed. If the insulation on the wire is damaged by wear, additional AC current will flow, as well as a possible DC current if a DC test signal is applied across the two electrodes. In any event, the impedance measured across the electrodes will decease with wear of the prothesis or damage to the insulated wire, and this decrease can be monitored by the control circuitry to determine when the prothesis has reached the predetermined wear threshold.

It should now be apparent that nearly any type of sensor can be implemented in the implantable biosensing transponder of the present invention, depending only upon the size of the particular sensor and the available space at the implantation site. As described above, the biosensing transponder can be configured for sensing or detecting particular parameter values related to an organism, including information related to the organism's tissue and information related to other implants within the organism.

Figure 12:
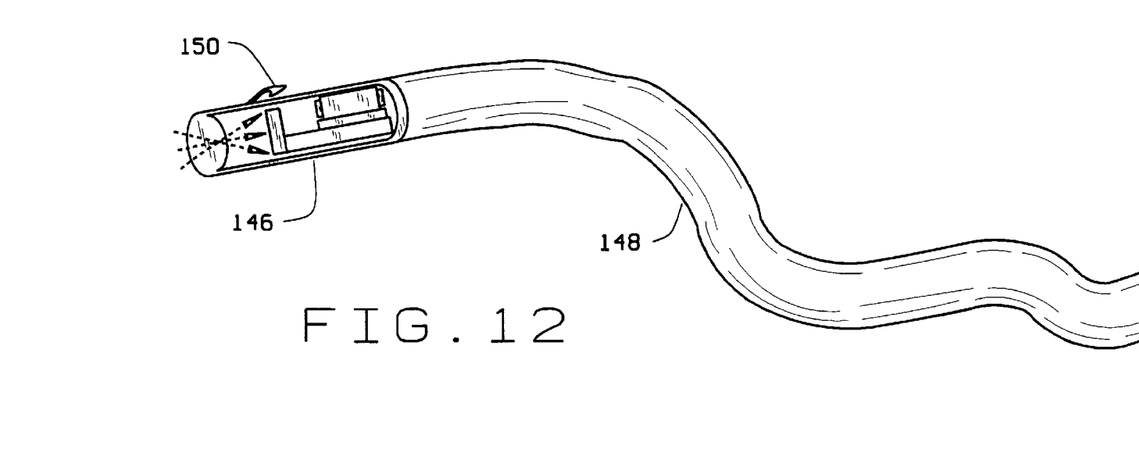
FIG. 12 illustrates a biosensing transponder attached to a flexible catheter.

Additionally, the biosensing transponder can be utilized with other types of devices that are used for performing medical assessments or procedures. For example, and as illustrated in FIG. 12, a biosensing transponder 146 containing an imager can be physically attached to a flexible intra-arterial catheter 148 to facilitate use of the catheter. Catheter 148 can then be fluoroscopically guided into a desired body cavity or vascular structure and addressed with a remote reader.

Alternatively, electromagnetic or ultrasonic signals emanating from transponder 146 can be used to locate the catheter during insertion if, for example, a hand-held reader is used to localize the signals. Moreover, various mechanical and/or magnetic latching mechanisms can be used to release transponder 146 from catheter 148 after the transponder has been guided to a desired location. Transponder 146 can also be configured for attachment to a desired tissue prior to being released from catheter 148, such as with a mechanical barb 150 or various other types of couplers.

In any embodiment of the present invention, including those described above, the control circuit can be configured to avoid a data collision with a like device. In other words, where multiple biosensing transponders are implanted within the interrogation range of a remote reader, it may be necessary to modify the control circuitry of each device so that, when interrogated, the devices transmit their respective data at different times.

This can be accomplished by providing a random delay generator in the control circuitry for delaying the transmission of data by an integer multiple of the time necessary to transmit an entire bit-stream of data, plus a slight extra delay. In this manner, it is unlikely that the data transmissions by multiple biosensing transponders will overlap. Such a delay generator can be implemented with simple digital circuits, such as shift-registers with exclusive-or feedback, to generate randomly varying time delays that will not be the same over time for a given biosensing transponder. Where feedback shift-register type delay generators are used which have their sequence of generated delay patterns programmed in a deterministic fashion, their starting bit sequences can be encoded during manufacturing or, instead, can be some of the bits of the biosensing transponder's identifying data.

Alternatively, the control circuitry can have a programmable delay, or can be configured with a predetermined hard-wired delay, and each biosensing transponder identified as to what delay length it has, perhaps by color coding. For a given number of biosensing transponders to be implanted within a relatively small volume, a non-repeating mix of different delays could be selected at the outset.

There are various changes and modifications which may be made to the invention as would be apparent to those skilled in the art. However, these changes or modifications are included in the teaching of the disclosure, and it is intended that the invention be limited only by the scope of the claims appended hereto, and their equivalents.

What is claimed is:

1. A passive biosensing device for implantation in an organism, said device including a dye having an optical property that can change in response to its environment, a photosensor for sensing the optical property of said dye, and a transponder for transmitting data corresponding to the sensed optical property to a remote reader, said dye being positioned for exposure to said organism when the device is implanted therein.

2. The device of claim 1 further including a dye isolated from the environment external to said device, said isolated dye being of a same type as said exposed dye, said device being configured for differential sensing of the dyes' optical properties.

3. The device of claim 2 further including an optical emitter for illuminating said dyes.

4. The device of claim 1 wherein said device includes a spectrophotometer for sensing the optical property of said dye, said spectrophotometer comprising said photosensor.

5. The device of claim 1 wherein said photosensor includes an optical filter for shielding said photosensor from selected wavelengths.

6. The device of claim 1 wherein said dye is a chemical sensitive dye.

7. The device of claim 1 wherein said device is configured to sense the optical property of said dye with said photosensor a fixed amount of time after illumination of said dye by a pulsed light source.

8. A passive biosensing device for implantation in an organism, said device including a first optical emitter for illuminating an environment external to said device, a photosensor for sensing an optical property from said external environment, and a transponder for transmitting data corresponding to the sensed optical property to a remote reader.

9. The device of claim 8 further including an electrical energy storage device, said first optical emitter receiving power from said transponder through a pulsatile discharge of said storage device.

10. The device of claim 8 further including a second optical emitter for illuminating said external environment, said first and second optical emitters emitting light at different wavelengths.

11. The device of claim 10 wherein said device is configured for alternately energizing said optical emitters.

12. The device of claim 10 wherein said device is configured for alternately energizing said optical emitters, sensing any backscattered optical energy with said photosensor, computing an oxygen saturation level for a portion of said organism based upon the output of said photosensor, and transmitting data indicative of the computed oxygen saturation level with said transponder.

13. The device of claim 8 further including a dye exposed to the external environment, said dye having an optical property that changes upon exposure to at least one type of chemical, said photosensor sensing the optical property of said dye.

14. The device of claim 8 wherein said device includes a spectrophotometer for sensing the optical property, said spectrophotometer comprising said photosensor.

15. The device of claim 8 wherein said photosensor includes an optical filter for shielding said photosensor from selected wavelengths.

16. The device of claim 8 wherein said device is configured to sense the optical property with said photosensor a fixed amount of time after illuminating the external environment with the first optical emitter.

17. A passive biosensing device for implantation in an organism, said device including a biosensor for sensing at least one parameter value related to said organism after implantation of said device and a transponder for transmitting data corresponding to the sensed parameter value to a remote reader, said device being configured to delay transmission of the data corresponding to the sensed parameter value when said transponder is energized to thereby prevent said device from transmitting data at the same time as an adjacent like device.

18. The device of claim 17 wherein said device is configured to delay transmission of said data by a predetermined period of time.

19. The device of claim 17 wherein said device is configured to randomly delay transmission of said data.

20. A remotely energizable biosensing device adapted for implantation in an organism, said device including a biosensor for sensing at least one parameter value related to said organism after implantation, said biosensor being connected to a transponder for coupling data corresponding to said parameter value to a remote reader, said biosensing device having data specific to said biosensor stored therein.

21. The biosensing device of claim 20 wherein said stored data includes calibration data for said biosensor.

* * * * *